United States Patent [19]

Haber et al.

[11] 3,978,072

[45] Aug. 31, 1976

[54] PHENYLENE BIS-N,N'(PYRIDONES)

[75] Inventors: Raphael Ralph G. Haber, Givatayim; Chaim Simonovitch, Rishon Letzion, both of Israel

[73] Assignee: Abic Ltd., Israel

[22] Filed: May 31, 1974

[21] Appl. No.: 475,194

Related U.S. Application Data

[62] Division of Ser. No. 241,847, April 6, 1972, Pat. No. 3,821,235.

[30] Foreign Application Priority Data

Apr. 14, 1971 Israel.................................... 36627

[52] U.S. Cl.......................................... 260/295.5 R
[51] Int. Cl.².................................... C07D 213/14
[58] Field of Search............... 260/295.5 R; 424/266

[56] References Cited
OTHER PUBLICATIONS

Ettel et al., Chem. Abstracts, vol. 46, 504g–506a, 1952.

*Primary Examiner*—Henry R. Jiles
*Assistant Examiner*—Bernard Dentz
*Attorney, Agent, or Firm*—Steinberg & Blake

[57] ABSTRACT

This invention relates to anti-inflammatory pyridone derivatives, particularly 2,6-dimethyl-1,4-dihydro-4-oxo-3,5 pyridine-dicarboxylates and derivatives thereof which have an anti-inflammatory action, as well as compositions therewith, use of these compounds for their anti-inflammatory effect, and production thereof. These 4-oxo pyridines of the present invention, refer to in the literature as 4-(1H)-pyridones are suitably prepared by reacting a 2,6-dimethyl-4-oxo 3,5 pyrone-dicarboxylate with an aniline in an acidic medium such as acetic acid.

3 Claims, No Drawings

PHENYLENE BIS-N,N'(PYRIDONES)

CROSS REFERENCE TO RELATED APPLICATION

This application is a divisional of our copending application Ser. No. 241,847 filed April 6, 1972, entitled "Pyridone Derivatives" now U.S. Pat. 3,821,235.

BACKGROUND OF THE INVENTION

The present invention relates to new anti-inflammatory and analgestic compositions.

There are known various anit-inflammatory agents, e.g. certain steroids (cortisone and its derivatives); acetyl salicylic acid (hereinafter called aspirin), butazolidin or indometacin. However, most of these known agents have unpleasant side effects, e.g. they cause ulcers.

It has thus been desirable to find compounds, which are useful anti-inflammatory agents, which are substantially as effective as the known anti-inflammatory agents but which have less unpleasant side effects.

M. Conrad and M. Guthzeit (Ber., 19(1886) and Ber., 20, 154 (1887) describe the preparation of 2,6-dimethyl-3,5-dicarboethoxy-4-pyridone, 2,6-dimethyl-3,5-dicarboethoxy-N-phenyl-4-pyridone, 2,6-dimethyl-3,5-dicarboethoxy-N-methyl-4-pyridone and 2,6-dimethyl-3,5-dicarboethoxy-N-acetyl-4-pyridone.

V. Ettel and J. Hebky, Coll. Czech.Chem.Com., 15, 639 (1950) and J. Hebky, Coll. Czech.Chem.Com., 16, 348 (1951) describe the synthesis of some of the same compounds as well as:

2,6-Dimethyl-3,5-dicarboethoxy-N-(p-hydroxyphenyl)-4-pyridone and its diacid;
2,6-Dimethyl-3,5-dicarboethoxy-N-(m-hydroxyphenyl)-4-pyridone and its diacid;
2,6-Dimethyl-3,5-dicarboethoxy-N-(4'-hydroxy-3',5'-dimethoxy phenyl)-4-pyridone and its diacid;
2,6-dimethyl-3,5-dicarboethoxy-N-(p-acetamidophenyl)-4-pyridone and its diacid;
1,4-bis-N,N'-(2',6'-dimethyl-3',5'-dicarboethoxy-4'-pyridone)-phenylene and its tetracid;
2,6-dimethyl-3,5-dicarboethoxy-N-(p-Iodophenyl)-4-pyridone and its diacid;
2,6-dimethyl-3,5-dicarboethoxy-N-(2',4'-Diiodophenyl)-4-pyridone and its diacid;
2,6-dimethyl-3,5-dicarboxy-N-(4'-hydroxy-3',5'-diiodophenyl)-4-pyridone
2,6-dimethyl-3,5-dicarboxy-N-(3'-hydroxy-2',4',6'-triiodophenyl)-4-pyridone.

Ettel & Hebky studied these compounds because of their interest in a novel X-Ray contrast agent for a similar use as the known diethanolamine salt of 3,5-diiodo-4-pyridone-N-acetic acid. They thus prepared and tested salts of the various above mentioned 2,6-dimethyl-N-(various Iodophenyl)-4-pyridone-3,5-dicarboxylic acids as X-Ray contrast agents.

We have now surprisingly found that certain esters of 2,6-dimethyl-N-substituted-4-pyridone-3,5-dicarboxylic acid have good anti-inflammatory properties substantially without having the unpleasant side effects of the known anti-inflammatory agents. Moreover, some of same pyridones have useful analgetic properties and some have beta-blocking properties. The free acids show substantially no activity while if the nitrogen carries no substituent the compounds are neurotoxic.

SUMMARY OF THE INVENTION

The present invention thus consists in pharmaceutical compositions comprising as active substance a pyridone derivative of the general formula I

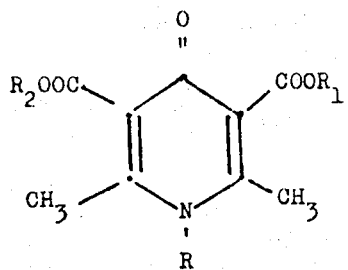

in which $R_1$ and $R_2$ stand for the same or different substituted or unsubstituted alkyl, alkylene, cycloalkyl or benzyl radicals and R stands for a phenyl radical which may be optionally substituted with one or more substituents selected from the group comprising alkyl, alkoxy, nitro, chloro, fluoro and dialkylamino radicals which may be the same or different.

Pyridones of general formula I comprise also bis-pyridones of general formula II

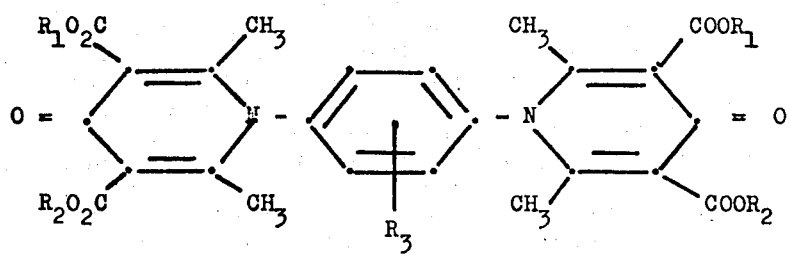

in which $R_1$ and $R_2$ have the same meaning as above and $R_3$ stands for hydrogen or for one or more substituents selected from the group comprising alkyl, alkoxy, nitro, chloro, fluoro, and substituted amino radicals which may be the same or different.

Many of the compounds of general formula I are new compounds. The present invention thus consists also in pyridone derivatives of general formula I wherein $R_1$ and $R_2$ have the same meaning as above and R stands for a phenyl radical substituted with one or more substituents selected from the group comprising alkyl, alkoxy, nitro, chloro, fluoro and dialkylamino radicals which may be the same or different.

The compounds of the present invention may be prepared by various suitable methods. A suitable process consists in reacting a pyrone of general formula III

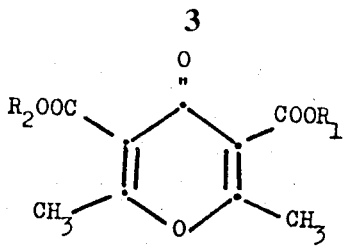

with an amine of general formula IV

R — NH$_2$ in which R, R$_1$ and R$_2$ have the same meaning as above. This reaction is preferably performed in acetic acid at elevated temperatures, e.g. 100°–130°C.

Compounds of general formula III may be prepared, for example, as described by Conrad and Guthzeit mentioned above.

In case that R$_1$ should be different from methyl or ethyl, an appropriate pyridone having R$_1$ equal R$_2$ being ethyl (or methyl) may be transesterified by boiling with an excess of the appropriate alcohol in the presence of an acid as catalyst and the lower boiling alcohol (methanol or ethanol) is removed by distillation. By this process only one group is transesterified.

Should both R$_1$ and R$_2$ have to be different from ethyl, the carboethoxy groups of the pyridone may be subjected to saponification and the compound obtained is esterified with the desired alcohol. Said esterification is preferably performed by first preparing the acid chloride, e.g. by reacting the 2,6-dimethyl-3,5-dicarboxy N-phenyl-4-pyridone with thionyl chloride in benzene and reacting thereafter the acid chloride with the desired alcohol.

The new compositions according to the present invention are preferably prescribed in the form of tablets, capsules, ampules, suppositoria, ointments, tinctures or solutions, said preparations being prepared in a conventional manner, i.e. by the addition of suitable binders, extenders, carriers, emulsifyers, solvents, other suitable therapeutic compounds and the like.

Compounds of general formula I showed anti-inflammatory properties when tested in the carrageenin induced oedema test on the hind paw of rats or in the cotton pellet granuloma test in rats. At present we found the 4-alkoxyphenyl derivatives to be the most active ones.

Significant anti-inflammatory activity and a good dose response was found at dosages between 50 mg/kg body weight and 200 mg/kg when administered orally or intraperitoneally.

Moreover, compounds of the pyridone derivatives of general formula I show a low ulcerogenic index at the effective anti-inflammatory dosage.

Some of the compounds demonstrated analgetic properties estimated by measuring the pain threshold in rats by the method of Randall and Selitto.

The toxicity of the tested compounds was quite low.

The present invention thus consists also in a method for the treatment of inflammations and/or for the relief of pain with a therapeutic dosage of a pyridone derivative of general formula I or with a composition containing same.

DESCRIPTION OF PREFERRED EMBODIMENTS

The following examples are given to further illustrate, but not restrict, the present invention.

EXAMPLE 1

2,6-dimethyl-3,5-dicarboethoxy-N-phenyl-4-pyridone was prepared cording to Conrad and Guthzeit (M. Conrad and M. Guthzeit, Chem. Ber., 19, 19-26, (1886)), by reacting 2,6-dimethyl-3,5-dicarboethoxy-4-pyrone (said compound will be called hereinafter "the pyrone") and aniline in acetic acid. (m.p. 170°C).

The compound has a good inhibitory effect on the development of Carrageenin induced Oedema in rats at a dose of 50 mg/kg and very good activity at the doses of 100 and 200 mg/kg, via oral or i.p. administration.

In doses of 100 mg/kg and 200 mg/kg the compound inhibited the cotton pellet granuloma formation in rats. The activity was greatly reduced with adrenolectromised rats were used in the experiments. a low ulceration index was recorded at doses between 50 mg/kg to 200 mg/kg in comparison with aspirin and indomethacin.

EXAMPLE 2

6.7 g. of o-toluidine were added to a solution of 8.5 g. of the pyrone in 60 ml. of glacial acetic acid. The mixture was stirred and heated at 110° for 1 hour. The mixture was then cooled and poured into 100 g. of crushed ice. The mixture obtained was neutralised with concentrated ammonia to pH 6 and the precipitate was filtered off, washed with water and dried yielding 8 g. of 2,6-dimethyl-3,5-dicarboethoxy-N-(2'-methylphenyl)-4-pyridone; m.p. 178°C.

The compound has a good inhibitory effect on the development of Carrageenin induced Oedema in rats at doses of 100 mg/kg and very good effects at 200 mg/kg. A very low ulceration index was recorded at a dose of 200 mg/kg in comparison to aspirin and indomethacin.

EXAMPLE 3

1.1 g. of 3-chloro aniline and 2 g. of the pyrone were dissolved in 10 ml. of glacial acetic acid. The mixture was stirred and heated for 15 minutes to 110°, then cooled and poured into 50 g. of ice and was thereafter neutralised with concentrated ammonia to pH 7. The precipitate was filtered off by suction, washed with water and dried to yield 3 g. of crude 2,6-dimethyl-3,5-dicarboethoxy-N-(3'-chlorophenyl)-4-pyridone; m.p. 204°–206°. After recrystallization from benzene the m.p. was 209-210°C.

At a dose of 200 mg/kg the compound exhibited moderate anti-inflammatory effect in the Carrageenin induced oedema.

In the same manner were prepared:
2,6-dimethyl-3,5-dicarboethoxy-N-(4'-chlorophenyl)-4-pyridone m.p. 129°:
2,6-dimethyl-3,5-dicarboethoxy-N-(4'-fluorophenyl)-4-pyridone m.p. 169°:
2,6-dimethyl-3,5-dicarboethoxy-N-(2'-fluorophenyl)-4-pyridone m.p. 112°:
2,6-dimethyl-3,5-dicarboethoxy-N-(3'-fluorophenyl)-4-pyridone m.p. 212°:

EXAMPLE 4

2 g. of pyrone were reacted with 1.5 g. of 4-n-butoxyaniline in the same manner as described in Example 2 to yield 3 g. of 2,6-dimethyl-3,5-dicarboethoxy-N-(4'-n-butoxyphenyl)-4-pyridone; m.p. 134°-5°C.

The compound has a good inhibitory effect on the development of Carrogeenin induced Oedema in rats at a dose of 100 mg/kg and a very good effect at a dose of 200 mg/kg. The compound also inhibited granuloma formation in intact and adrenalectomized rats at the doses of 100 mg/kg and 200 mg/kg.

A low ulcerogenic index was recorded at the doses described above. At a dose of 200 mg/kg the compound had a good effect on adjuvant arthritis in rats, as compared to indomethacin. A good analgesic activity was observed at a dose of 200 mg/kg as compared to aminopyrine.

The following compounds were prepared in the same manner:

2,6-dimethyl-3,5-dicarboethoxy-N-(4'-ethoxyphenyl)-4-pyridone; m.p. 165°
2,6-dimethyl-3,5-dicarboethoxy-N-(4' methoxyphenyl)-4-pyridone; m.p. 159-160°
2,6-dimethyl-3,5-dicarboethoxy-N-(4'-isobuthoxyphenyl)4-pyridone; m.p. 110°
2,6-dimethyl-3,5-dicarboethoxy-N-(4'-isopentyloxyphenyl)4-pyridone; m.p. 168°
2,6-dimethyl-3,5-dicarboethoxy-N-(4'-heptyloxyphenyl)4-pyridone; m.p. 102°
2,6-dimethyl-3,5-dicarboethoxy-N-(4'-octyloxyphenyl)4-pyridone; m.p. 86°
2,6-dimethyl-3,5-dicarboethoxy-N-(4'-tetradecyloxyphenyl)-4-pyridone; m.p. 87°
2,6-dimethyl-3,5-dicarboethoxy-N-(4'-octadecyloxyphenyl)4-pyridone; m.p. 90°
2,6-dimethyl-3,5-dicarboethoxy-N-(4'-decyloxyphenyl)4-pyridone; m.p. 87°
2,6-dimethyl-3,5-dicarboethoxy-N-(4'-cyclohexyloxyphenyl)4-pyridone; m.p. 170°
2,6-dimethyl-3,5-dicarboethoxy-N-(4'-heptadecyloxyphenyl)4-pyridone; m.p. 85°
2,6-dimethyl-3,5-dicarboethoxy-N-(4'-pentyloxyphenyl)4-pyridone; m.p. 92°
2,6-dimethyl-3,5-dicarboethoxy-N-(4'(3"hexyloxy)-phenyl)4-pyridone; m.p. 145°
2,6-dimethyl-3,5-dicarboethoxy-N-(4'-pentadecyloxyphenyl)4-pyridone; m.p. 95°
2,6-dimethyl-3,5-dicarboethoxy-N-(4'(4"heptyloxy)-phenyl)4-pyridone; m.p. 116°
2,6-dimethyl-3,5-dicarboethoxy-N-(4'(2"heptyloxy)-phenyl)4-pyridone; m.p. 90°
2,6-dimethyl-3,5-dicarboethoxy-N-(4'(4"octyloxy)-phenyl)4-pyridone; m.p. 104°
2,6-dimethyl-3,5-dicarboethoxy-N-(4'(3"pentyloxy)-phenyl)4-pyridone; m.p. 172°
2,6-dimethyl-3,5-dicarboethoxy-N-(4'propoxyphenyl)4-pyridone; m.p. 122°
2,6-dimethyl-3,5-dicarboethoxy-N-(4'hexyloxyphenyl)4-pyridone; m.p. 104°
2,6-dimethyl-3,5-dicarboethoxy-N-(2'4'-dimethoxy)4-pyridone; m.p. 178°

In the Carrogeenin induced Oedema in the rat the compounds described above showed good to very good activity at a dose of 200 mg/kg and some have moderate to good angesic activity at the same dose.

EXAMPLE 5

1.25 g. of the pyrone was reacted with 0.4 g. of p-toluidine in the same manner as described in Example 2 to yield 1.2 g. of 2,6-dimethyl-3,5-dicarboethoxy-N-(4'-methylphenyl)-4-pyridone; m.p. 110°.

At a dose of 200 mg/kg the compound showed moderate anti-inflammatory effect on the Carrageenin induced oedema in rats.

EXAMPLE 6

1.25 g. of the pyrone was reacted with 2.3 g. of dimethyl aniline in the same manner as described in Example 2 to yield 1.7 g. of 2,6-dimethyl-3,5-dicarboethoxy-N-(2',3'-dimethyl-phenyl)-4-pyridone; m.p. 100° (recrystallised from benzene petrol-ether 40°-60°C)

At a dose of 200 mg/kg the compound showed moderate anti-inflammatory effect on the Carrageenin induced oedema in rats.

EXAMPLE 7

2 g. of the pyrone and 1.1 g. of 4-nitroaniline were dissolved in 20 ml. of acetic acid and the mixture was stirred and heated to 110° for 24 hours. Thereafter the mixture was cooled and poured into 100 g. of crushed ice. The suspension was neutralised to pH 7 with concentrated ammonia and the crystals obtained were filtered off and dried.

Yield: 1.5 g. of 2,6-dimethyl-3,5-dicarboethoxy-N-(4'-nitrophenyl)-4-pyridone; m.p. 195°.

At a dose of 200 mg/kg the compound showed good anti-inflammatory effect on the Carrageenin induced oedema in rats.

EXAMPLE 8

2 g. of the pyrone and 1.32 g. of p-dimethylamino aniline were dissolved in 20 ml. of acetic acid and the mixture was stirred and heated to 110° for 30 minutes. Then it was cooled, poured on 100 g. crushed ice and neutralised to pH 7 with concentrated ammonia. The oil that separated was extracted with chloroform. The obtained extracts were dried over magnesium sulphate and the chloroform was dissolved off in vacuo. The residue was crystallised from ethanol water to yield 1.5 g. of 2,6-dimethyl-3,5-dicarboethoxy-N-(4'-dimethylaminophenyl)-4-pyridone; m.p. 140°.

At a dose of 200 mg/kg the compound showed weak anti-inflammatory effect on the Carrageenin induced oedema in rats.

EXAMPLE 9

2 g. of the pyrone were reacted with 1.32 g. of 4-diethyl amino aniline in the same manner as described in Example 8 to yield 2,6-dimethyl-3,5-dicarboethoxy-N-(4'-diethylaminophenyl)-4-pyridone; m.p. 138°.

At a dose of 200 mg/kg the compound showed good anti-inflammatory effect on the Carrageenin induced oedema in rats.

EXAMPLE 10

4 g. of 2,6-dimethyl-3,5-dicarboethoxy-N-phenyl-4-pyridone (prepared as described in Example 1) were dissolved in 20 ml. of benzyl alcohol, 4 drops of concentrated $H_2SO_4$ were added and the mixture was stirred and heated for 7 hours at 130°, at the same time distilling off the produce ethanol. The benzyl alcohol solution was washed with a saturated solution of sodium bicarbonate and the slurry was extracted several times with chloroform. The extracts were combined and dried over magnesium sulphate, and the chloroform was distilled off in vacuo. The oily residue was dissolved in 50 ml. of ether and 50 ml. of petrolether 40'-60° were added. After cooling in a dry ice-acetone bath and scratching, 2,5g. of 2,6-dimethyl-3-carboethoxy-5-carbobenzyloxy-N-phenyl-4-pyridone, m.p. 142° were obtained.

At a dose of 200 mg/kg the compound showed weak anti-inflammatory effect on the Carrageenin induced oedema in rats.

EXAMPLE 11

1.5 g. of 2,3-dimethyl-3,5-dicarboethoxy-N-phenyl-4-pyridone (prepared as described in Example 1) was dissolved in 45 ml. of butanol, 2 drops of concentrated sulfuric acid were added and the mixture was stirred and heated at 100° for seven hours, and the produced ethanol was distilled off simultaneously. The mixture was cooled, transferred into a separatory funnel and shaked with a saturated solution of sodium bicarbonate. The organic phase was separated and evaporated to dryness. The residue was crystallised from isopropanol to yield 0.5 g. of 2,6-dimethyl-3-carboethoxy-5-carbobutoxy-N-phenyl-4-pyridone; m.p. 110°.

At a dose of 200 mg/kg the compound showed moderate anti-inflammatory activity on the Carrageenin induced oedema in rats.

EXAMPLE 12

The tetra ethyl ester of phenylene-1,4-bis-N,N'-(2,6-dimethyl-3,5-dicarboxylic acid-4-pyridone) was prepared according to Ettel (V. Ettel and J. Hebky, Coll. Czech. Chem. Commun., 15, 639–651 (1950)) by reacting p-phenylene diamine with the pyrone in acetic acid.

The compound has a good inhibitory effect on the development of Carrageenin induced Oedema in rats at a dose of 100 mg/kg and very good effect at a dose of 200 mg/kg. The compound inhibited granuloma formation in intact and adrenalectomised rats at doses of 100 mg/kg and 200 mg/kg. Low ulcerogenic indexes was recorded at the doses described above as compared to indomethacin. A very good analgesic activity was observed at a dose of 200 mg/kg as compared to amino pyrine.

In a similar manner utilising as starting material the appropriate diamine the following compounds were prepared:

a. 1,4-bis-N,N'-(2,6-dimethyl-3,5-dicarboethoxy-4'-pyridone-N)-2-methyl-phenylene; m.p. 313° b. 1,4-bis-N,N'-(2,6-dimethyl-3,5-dicarboethoxy-4'-pyridone-N)-2-methoxy-phenylene; m.p. 315° c. 1,4-bis-N,N'-(2,6-dimethyl-3,5-dicarboethoxy-4'-pyridone-N)-2,5-dimethyl-phenylene; m.p. 320°

EXAMPLE 13

2,6-dimethyl-N-phenyl-4-pyridone-3,5-dicarboxylic acid was prepared according to Conrad and Guthzeit (M. Conrad and M. Guthzeit, Chem. Ber., 20, 154–163 (1887)).

A solution of 1 g. of the diacid and 1,23 g. of thionyl chloride in 50 ml. of benzene was refluxed for 4 hours. The solvent was removed in vacuo. To the residue were added 50 ml. of anhydrous methanol and the mixture was refluxed for 1 hour. The methanol was removed in vacuo, water was added and the acid solution was neutralised to pH 6.5. The material which had been precipitated was filtered off and dried in the air to yield 2,6-dimethyl-3,5-dicarbomethoxy-N-phenyl-4-pyridone; 88.5% yield; m.p. 215°.

EXAMPLE 14

A solution of 1 g 2,6-dimethyl-3,5-carboxy-N-phenyl-4-pyridone and 1.23 g. of thionyl chloride in 50 ml of benzene was refluxed for four hours. The solvent was removed in vacuo. To the residue were added 50 ml. of isopropyl alcohol and the mixture was refluxed for 1 hour. The solvent was removed in vacuo, water was added and the solution was neutralised to pH 6.5. The solid which precipitated was filtered off and dried in the air, to yield 2.5 g of 2,6-dimethyl3,5-dicarbo-isopropyloxy-N-phenyl-4-pyridone; m.p. 185°.

In the same way were prepared utilising the appropriate alcohols:

a. 2,6-dimethyl-3,5-dicarbo cyclohexyloxy-N-phenyl-4-pyridone; m.p. 80°.

b. 2,6-dimethyl-3,5-dicarbo (1'-propene)-yloxy-N-phenyl-4-pyridone; m.p. 140°, c. 2,6-dimethyl-3,5-dicarbo isobutyloxy-N-phenyl-4-pyridone; m.p. 200°C d. 2,6-dimethyl-3,5-dicarbo butyloxy-N-phenyl-4-pyridone; m.p.

EXAMPLE 15

Tablets of a pyridone can be prepared in the following manner: Blend together 400 g of 2,6-dimethyl-3,5-dicarboethoxy-N-(4'-heptyloxy phenyl)-4-pyridone-(active compound) and 100 g lactose with starch paste (made of 25 g starch) dry in the oven at 45°C overnight. Pass the dry granulation through a No. 16 stainless steel screen. To the screened granulation add 2.7 g stearic acid and 50 g talcum(previously screened through a size 40 stainless steel screen) and compress to tablets.

In this way each tablet contains:

| Active compound | 400 mg |
| Lactose | 100 mg |
| Starch | 25 mg |
| Stearic acid | 2.7 mg |
| Talcum | 50 mg |

EXAMPLE 16

Capsules of a pyridone can be prepared in the following manner: Blend well 400 g of 2,6-dimethyl-3,5-dicarboethoxy-N-(4'-heptyloxyphenyl)4-pyridone (Active compound) and 200 g lactose and 60 g of Cabosil and fill into capsules.

Each capsule contains:

| Active compound | 400 mg |
| Lactose | 200 mg |
| Cabosil (Fumed silica of Cabot Corp.) | 6 mg |

EXAMPLE 17

Tablets of a pyridone can also be prepared in the following manner: Blend 400 g of 2,6-dimethyl-2,5-dicarboethoxy-N-(4'-N-buthoxy phenyl) -4-pyridone (active compound) and 200 g of starch and make ½inch slugs. Pass the slugs through a Fitz mill.

Dust on 1.5 g Mg stearate on the granulation and compress on a BB2, press into tablets using flat level edge 12 mm punches.

Each tablet contains:

| Active compound | 400 mg |
| Starch | 200 mg |

| | |
|---|---|
| Mg stearate | 1.5 mg |

EXAMPLE 18

Suppositories of a pyridone can be prepared as follows: Melt at 50°C 16 g of cocoa butter, add 40 mg of 2,6-dimethyl-2,5-dicarboethoxy-N-(4'-n-buthoxy phenyl)-4-pyridone, homogenize if necessary, pour into moulds and allow to congeal. Extrude suppositories and wrap.

EXAMPLE 19

Ointment of a pyridone can be prepared in the following manner: In 80 ml of boiling water dissolve 200 mg of methyl parabene and 50 mg of propyl parabene, cool to 70°C. In a separate container melt 10 g of cetostearyl alcohol, add 400 mg of 2,6-dimethyl-3,5-dicarboethoxy-N-(4'-(3'' pentyloxy)-phenyl)-4-pyridone (active compound) and heat to 70°C. Add the water phase into the oil phase with vigorous agitation. Continue agitation until temperature drops to 45°C. Allow mixture to cool to room temperature, and package into appropriate size tubes.

The formula thus obtained is:

| | |
|---|---|
| Active compound | 0.4% |
| ceto-stearyl alcohol | 10% |
| methyl parabene | 0.2% |
| propyl parabene | 0.05% |
| water quantity sufficient to 100% | |

EXAMPLE 20

A suspension of a pyridone may be prepared in the following manner: Into 50 ml. of boiling water dissolve 200 mg of methyl parabene and 50 mg. of propyl parabene and then add with vigorous agitation carbomethylcellulose (CMC) (100 mg), vee gum (5 g)(Vee gum stands for magnesium aluminium silicate of Vanderbilt), sugar (30 g) and 70% solution of Sorbo (20g)(70%Sorbitol). Continue agitation until gums are fully hydrated. Dust on the 2,6-dimethyl-3,5-dicarboethoxy-N-(4'-3''-pentyloxy)-4-pyridone)-(active compound) (2 g), mix well and homogenize.

The suspension thus obtained consists of:

| | |
|---|---|
| Active compound | 2% |
| Vee Gum | 5% |
| CMC | 0.1% |
| Methyl parabene | 0.2% |
| Propyl parabene | 0.5% |
| Sorbitol (70% solution) | 20% |
| Flavoured water sufficient to 100% | |

Flavoured water sufficient to 100%

We claim:

1. A pyridone derivative selected from the group consisting of 1,4-bis-N,N'-(2'',6''-dimethyl-3',5'-dicarboethoxy-4'-pyridone-N)-2,5-dimethylphenylene and 1,4-bis-N,N'-(2'',6''-dimethyl-3',5'-dicarboethoxy-4'-pyridone-N)-2-methoxyphenylene.

2. Pyridone derivative according to claim 1 wherein said compound is 1,4-bis-N, N'-(2'', 6''-dimethyl-3', 5'-dicarboethoxy-4'-pyridone-N)-2-methoxyphenylene.

3. Pyridone derivative according to claim 1 wherein said compound is 1,4-bis-N, N'-(2'',6''-dimethyl-3', 5'-dicarboethoxy-4'pyridone-N)-2,5-dimethylphenylene.

* * * * *